(12) United States Patent
Neumann

(10) Patent No.: US 11,443,424 B2
(45) Date of Patent: Sep. 13, 2022

(54) ARTIFICIAL INTELLIGENCE METHODS AND SYSTEMS FOR ANALYZING IMAGERY

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 50 days.

(21) Appl. No.: 16/837,007

(22) Filed: Apr. 1, 2020

(65) Prior Publication Data

US 2021/0312611 A1 Oct. 7, 2021

(51) Int. Cl.
*G06T 7/00* (2017.01)
*G06N 20/00* (2019.01)
*G06N 5/04* (2006.01)

(52) U.S. Cl.
CPC ........... *G06T 7/0012* (2013.01); *G06N 5/04* (2013.01); *G06N 20/00* (2019.01); *G06T 2207/20081* (2013.01); *G06T 2207/30008* (2013.01); *G06T 2207/30016* (2013.01); *G06T 2207/30101* (2013.01)

(58) Field of Classification Search
CPC ......... G06T 7/0012; G06T 2207/30101; G06T 2207/20081; G06T 2207/30008; G06T 2207/30016; G06N 5/04; G06N 20/00
See application file for complete search history.

(56) References Cited

U.S. PATENT DOCUMENTS

| | | | |
|---|---|---|---|
| 9,504,420 B2 | 11/2016 | Davis et al. | |
| 10,192,033 B2 | 1/2019 | Kurtz et al. | |
| 10,366,487 B2 | 7/2019 | Kim | |
| 2007/0070038 A1* | 3/2007 | Hoffberg | G16H 40/67 345/156 |
| 2012/0124122 A1* | 5/2012 | el Kaliouby | G06Q 10/101 709/202 |
| 2014/0121540 A1 | 5/2014 | Raskin | |
| 2015/0157243 A1 | 6/2015 | Do et al. | |
| 2016/0034663 A1 | 2/2016 | Nino et al. | |
| 2018/0055384 A1 | 3/2018 | Ambili et al. | |
| 2018/0220952 A1 | 8/2018 | Lee et al. | |
| 2018/0232883 A1* | 8/2018 | Sethi | G06K 9/6267 |
| 2018/0289334 A1 | 10/2018 | De Brouwer et al. | |
| 2019/0065970 A1 | 2/2019 | Bonutti et al. | |
| 2019/0110753 A1* | 4/2019 | Zhang | G06N 3/084 |
| 2019/0223780 A1 | 7/2019 | O'Brien et al. | |

(Continued)

OTHER PUBLICATIONS https://www.skinvision.com/service.

*Primary Examiner* — Omar S Ismail
(74) *Attorney, Agent, or Firm* — Caldwell Intellectual Property Law

(57) ABSTRACT

An artificial intelligence system for analyzing imagery, the system comprising a computing device, the computing device designed and configured to receive a plurality of photographs related to a human subject; analyze the plurality of photographs to identify a conditional indicator contained within the plurality of photographs; generate a classification algorithm utilizing the conditional indicator, wherein the classification algorithm utilizes the conditional indicator as an input and outputs a conditional profile; and determine a conditional status of the human subject utilizing the conditional profile.

18 Claims, 6 Drawing Sheets

(56) References Cited

U.S. PATENT DOCUMENTS

| | | |
|---|---|---|
| 2019/0239789 A1 | 8/2019 | Jung et al. |
| 2019/0333220 A1 | 10/2019 | DeLuca et al. |
| 2020/0219295 A1* | 7/2020 | el Kaliouby ......... G06K 9/6273 |
| 2021/0327585 A1* | 10/2021 | Narayanan ............. G16H 50/20 |

* cited by examiner

ARTIFICIAL INTELLIGENCE METHODS AND SYSTEMS FOR ANALYZING IMAGERY

FIELD OF THE INVENTION

The present invention generally relates to the field of artificial intelligence. In particular, the present invention is directed to artificial intelligence methods and systems for analyzing imagery.

BACKGROUND

Conditions can be hidden and remain undetected for years on end. This can be quite challenging for individuals, who cannot appropriately seek treatment and manage these hidden problems. This can be further frustrated by an inability to intervene and reverse disease early.

SUMMARY OF THE DISCLOSURE

In an aspect, an artificial intelligence system for analyzing imagery, the system comprising a computing device, the computing device designed and configured to receive a plurality of photographs related to a human subject; analyze the plurality of photographs to identify a conditional indicator contained within the plurality of photographs; generate a classification algorithm utilizing the conditional indicator, wherein the classification algorithm utilizes the conditional indicator as an input and outputs a conditional profile; and determine a conditional status of the human subject utilizing the conditional profile.

In an aspect, an artificial intelligence method of analyzing imagery, the method comprising receiving by a computing device, a plurality of photographs related to a human subject; analyzing by the computing device, the plurality of photographs to identify a conditional indicator contained within the plurality of photographs; generating by the computing device, a classification algorithm utilizing the conditional indicator, wherein the classification algorithm utilizes the conditional indicator as an input and outputs a conditional profile; and determining by the computing device, a conditional status of the human subject utilizing the conditional profile.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to artificial intelligence systems and methods for analyzing imagery. In an embodiment, a computing device analyzes a plurality of photographs to identify conditional profiles of users. Conditional profiles are generated using a classification algorithm, and additional machine-learning processes.

Figure 1:
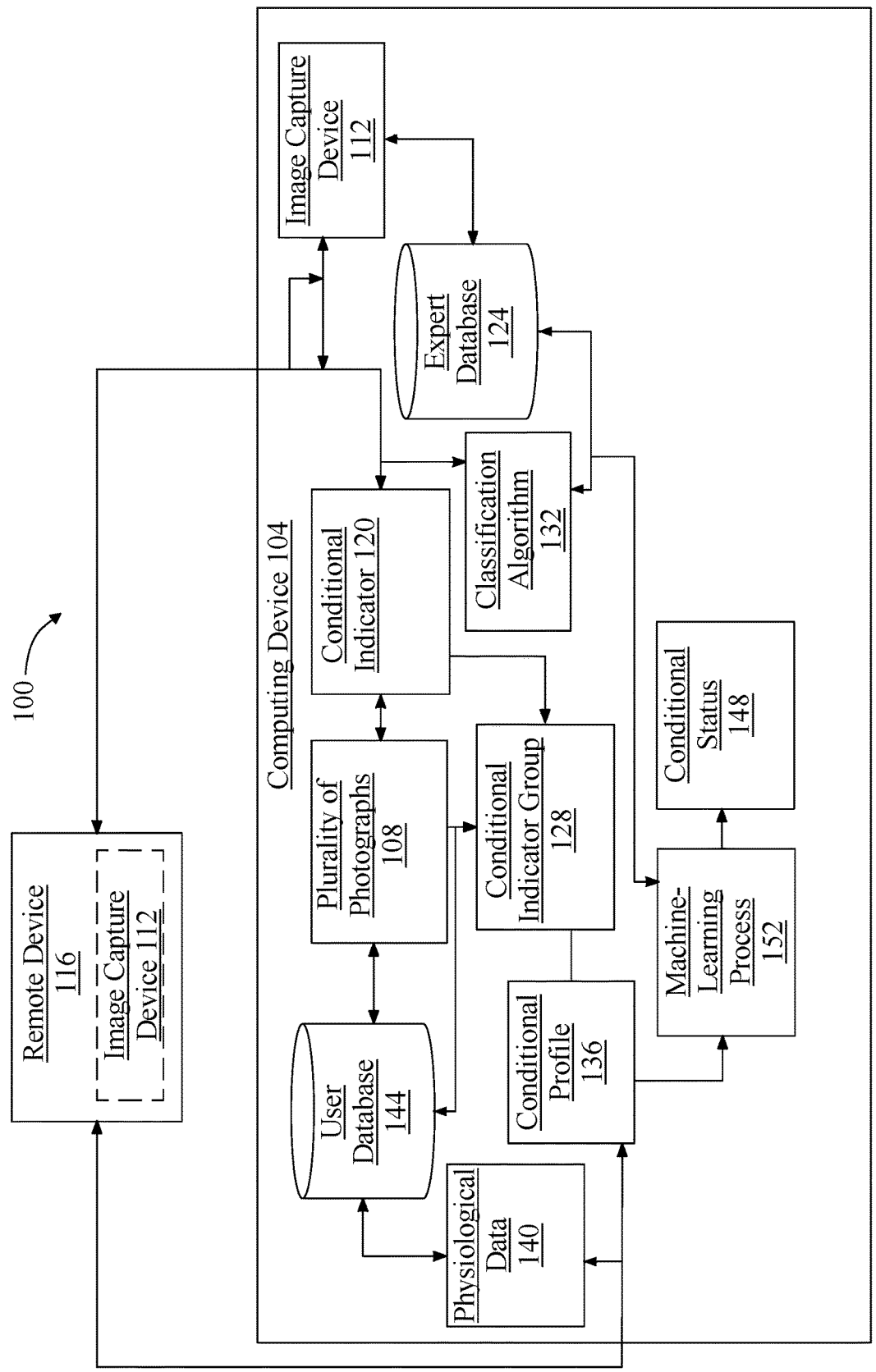
FIG. 1 is a block diagram illustrating an exemplary embodiment of an artificial intelligence system for analyzing imagery.

Referring now to FIG. 1, an exemplary embodiment of an artificial intelligence system 100 for analyzing imagery is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to receive a plurality of photographs 108 relating to a human subject. A "photograph," as used in this disclosure, is an image created by light falling on a photosensitive surface. A photosensitive surface may include photograph film, an electronic image sensor such as a charge-coupled device (CCD), and/or an electronic image sensor such as a complementary metal oxide semiconductor (CMOS) chip. A photograph may be created using a camera. A "camera," as used in this disclosure, is an optical instrument used to record images. A camera may include for example, a single-lens reflex (SLR) camera, a large format camera, a medium format camera, a compact camera, a rangefinder camera, a motion picture camera, a digital camera, and the like.

With continued reference to FIG. 1, computing device 104 is configured to receive at an image capture device 112 located on computing device 104, a wireless transmission from a remote device containing a plurality of photographs 108 related to a human subject. An "image capture device," as used in this disclosure, is any device suitable to take a photograph and/or video of a human subject. Image capture device 112 may include for example, a camera, a mobile phone camera, a scanner, and the like. A "human subject," as used in this disclosure, includes any user of system 100. A remote device 116, may include without limitation, a display in communication with computing device 104, where a display may include any display as described herein. Remote device 116 may include an additional computing device, such as a mobile device, laptop, desktop, computer and the like. In an embodiment, image capture device 112 may be located on a remote device 116 operated by a human subject, such as a camera located on a remote device 116 such as a mobile phone or laptop. In such an instance, a user may take a plurality of photographs 108 utilizing a remote device 116. In an embodiment, a third-party, such as a family member, friend, spouse, co-worker, and/or acquittance of the user may take one or more photographs of the user utilizing a remote device 116. For example, a user's boyfriend may take a series of photographs of the user utilizing an image capture device 112 such as a camera located on the user's mobile phone. Image capture device located on computing device 104 may receive a wireless transmission from a remote device 116 containing a plurality of photographs 108 related to a human subject utilizing any network methodology as described herein.

With continued reference to FIG. 1, a photograph may be related to a human subject when the photograph contains an image of the human subject. For example, a photograph may contain an image of a user's entire body, or an image of certain parts of a user's body such as an image of the user from the head and up. A photograph may be related to a human subject when the photograph was taken by the human subject. For example, a photograph taken by a user showing the inside of the user's kitchen is related to the human subject. In yet another non-limiting example, a photograph taken by a user showing the several of user's friends is related to the human subject. A photograph may be related to a human subject when the photograph contains an image showing any property owned and/or operated by the human subject. For example, a photograph may be related to a user when the photograph shows an image of a house or dwelling that the user lives in. In yet another non-limiting example, a photograph may be related to a human subject when the photograph shows A photograph may be related to a human subject when the photograph contains an image showing any food, nutrition, and/or supplements intended to be consumed and/or ingested by a human subject. For instance and without limitation, a photograph may contain an image of a meal a human subject cooked at home and intends to consume. In yet another non-limiting example, a photograph may contain an image of a meal that a user ordered from a restaurant. A photograph may be related to a human subject when the photograph contains an image showing a social event and/or social activity that a user participates in. For instance and without limitation, a photograph may contain an image showing a user participating in a group fitness class or partaking in a hobby such as knitting. In yet another non-limiting example, a photograph may contain an image of one or more materials that a user may use to participate in a hobby such as a photograph containing an image of a bike that the user utilizes to go on bike rides.

With continued reference to FIG. 1, computing device 104 is configured to receive a plurality of photographs 108 related to the human subject from a social networking platform. A "social networking platform," as used in this disclosure, is any website and/or application that enables a user to create and share content, and/or to participate in social networking. A social networking platform may include computer-mediated technologies that facilitate the creation or sharing of information, ideas, career interests and other forms of expression through virtual communities and networks. A social networking platform may contain user-generated content such as text posts, comments, photographs, videos, and/or data generated through online interactions. A social networking platform may allow a user to create an individual profile that identifies background demographic information about the user, such as for example the user's name, neighborhood where the user lives, highest education that the user has achieved, work and/or employment history, marital status, reviews of the user by third-parties such as friends, colleagues, neighbors and the like. For instance and without limitation, a social networking platform may include an application such as but not limited to, FACEBOOK, INC. of Menlo Park, Calif.; YOUTUBE of San Bruno, Calif.; WHATSAPP of Menlo Park, Calif.; INSTAGRAM of Menlo Park, Calif.; TIKTOK of Shanghai, China; TWITTER of San Francisco, Calif.; LINKEDIN of Sunnyvale, Calif.; SNAPCHAT of Santa Monica, Calif.; PINTEREST of San Francisco, Calif. and the like. Computing device 104 may receive a plurality of photographs 108 from a social networking platform utilizing any network methodology and/or network transmission as described herein. In an embodiment, computing device 104 may extract a plurality of photographs 108 pertaining to a user from one or more social networking platforms utilizing any data scraping techniques. Data scraping may include extracting data from human-readable output coming from another program. In an embodiment, computing device 104 may scrape data from one or more websites, utilizing a web scraper such as an application programming interface (API). An API includes any computing interface to a software component or a system that defines how other components and/or other systems can use it. An API may define different kinds calls or requests that can be made, how to make them, data formats that should be used, conventions to follow and the like. An API may also include extension mechanisms so that users can extend existing functionality in various ways and to varying degrees. An API may be customized, and/or designed based on an industry standard to ensure interoperability. In an embodiment, an API may allow for the combination of multiple APIs into a new application known as mashups, which may facilitate the sharing of content and data between communities and applications. A web scraper may contain data feeds from web servers such as JavaScript Object Notation (JSON) that may be used as a transport storage mechanism between a computing device 104 and a webserver. A web scraper may utilize one or more techniques in document object model (DOM) parsing, computer vision, and/or natural language processing to simulate human processing that occurs when viewing a webpage to extract useful and/or meaningful information. In an embodiment, computing device 104 may receive a plurality of photographs 108 related to a human subject from a social networking platform based on one or more permissions controlled by the human subject. For instance and without limitation, the human subject may allow computing device 104 to retrieve photographs from a first social networking platform but not a second social networking platform. In yet another non-limiting example, a user may allow computing device 104 to retrieve photographs from a first social networking platform between a certain time period, such as between May through August during a certain year, or only during a specific year such as during the year 2019.

With continued reference to FIG. 1, computing device 104 is configured to analyze a plurality of photographs 108 to identify a conditional indicator 120 contained within the plurality of photographs 108. A "conditional indicator," as used in this disclosure, is a determinant of a user's health; conditional indicator may be any determinant of the user's health. A determinant of health, as used herein, is a factor that impacts a person's health and wellness; determinant may include any factor that can have an impact on one's health and wellness. A determinant of health may include factors such as where a user lives, the state of a user's home environment, genetics, income, education level, social relationships with family, friends, acquaintances and the like, race, gender, age, nutrition, social status community involvement and/or engagement, major life events, physical activity levels, smoking status, alcohol and drug use, access to healthcare, health behaviors, and the like. For instance and without limitation, a conditional indicator 120 may identify one or more determinants of health contained within an image, such as a photograph that contains an image of a user smoking cigarettes and drinking alcohol. In yet another non-limiting example, a conditional indicator 120 may reveal if a user is surrounded by other people in any photographs, such as if the user is pictured in a circle of friends or if they are routinely pictured being alone. A conditional indicator 120 may identify any nutritional behaviors and/or eating patterns of a user. For example, a conditional indicator 120 may identify different types of food, and/or nutrients that a user consumes, such as a plurality of photographs 108 that show that the user frequently eats meals from fast food restaurants that contain very few if any vegetables. A conditional indicator 120 may identify nutritional behaviors such as if a user routinely cooks meals at home, orders food to go from restaurants, and/or eats meals at restaurants. A conditional indicator 120 may indicate one or more social habits and/or factors pertaining to a user, such as if a user is a member of a church or religious organization, if a user participates in social activities with friends and the like. A conditional indicator 120 may indicate one or more fitness habits of a user, such as if a user is pictured engaging in physical activity such as by running or lifting weights. A conditional indicator 120 may identify one or more social determinants of a user's health, such as the user's age, race, and/or gender. A conditional indicator 120 may identify one or more behavior characteristics of a user, such as any photographs that contain an image of the user may reflect if the user is smiling or posing happily and for the camera, which may indicate that the person is extroverted and socially connected, while an image of the user who is hiding from the camera may indicate that the user is shy and introverted. A conditional indicator may indicate one or more internal determinants of a user's health. For example, a conditional indicator that reflects a user who frequently within a plurality of photographs 108 has pale skin and bags under the user's eyes may be suffering from a medical condition such as fatigue and/or anemia. In yet another non-limiting example, a user with cracks in corner of the user's lips may be suffering from a Vitamin B deficiency.

With continued reference to FIG. 1, computing device 104 may identify one or more conditional indicator 120 contained within a plurality of photographs 108 based on expert input. One or more experts may provide input that may be stored within expert database 124. Expert database 124 may include any data structure for ordered storage and retrieval of data, which may be implemented as a hardware or software module. An expert database 124 may be implemented, without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 1, computing device 104 is configured to identify a conditional indicator group 128 identified within a plurality of photographs 108. A "conditional indicator group," as used in this disclosure, is any determinant of health that has a shared commonality and/or any determinant of health that is repeatedly contained within the plurality of photographs. A determinant of health may have a shared commonality when the determinant of health may have a common root cause, or when two or more conditional indicator 120 may contribute to the same determinant of health. For instance and without limitation, a first conditional indicator 120 such as alcohol use, and a second conditional indicator 120 such as marital status may both relate to a conditional indicator group 128 such as social determinants of health. In yet another non-limiting example, a first conditional indicator 120 such as cooking habits and a second conditional indicator 120 such as recent meals consumed by a user, and a third condition indicator such as supplements consumed by a user, may all relate to a conditional indicator group 128 of nutritional determinants of health. A conditional indicator group may contain a determinant of health that is repeatedly contained within the plurality of photographs, such as fitness activities that a user engages in may be repeatedly contained within a plurality of photographs, and as such, a conditional indicator group may identify the repeated photographs containing fitness activities as belonging to a conditional indicator group 128 of exercise determinants of health. In yet another non-limiting example, a conditional indicator group may contain a determinant of health that is repeatedly contained within the plurality of photographs, such as pictures of meals that a user consumes as belonging to a conditional indicator group 128 of nutritional determinants of health. Computing device 104 may identify one or more conditional indicator group 128 utilizing input contained within expert database 124. Computing device 104 generates a label identifying a conditional indicator group 128. A "label," as used in this disclosure, is data, including any numerical, symbolic, and/or character data indicating the group that a conditional indicator 120 belongs to. In an embodiment, a conditional indicator may belong to one or more groups. For instance and without limitation, a conditional indicator 120 such as meal patterns may belong to a first conditional indicator group 128 such as nutritional determinants of health and a second conditional indicator group 128 such as social determinants of health. In yet another non-limiting example, a conditional indicator 120 such as exercise habits may belong to a first conditional indicator 120 such as health behavior determinants of health, and a second conditional indicator 120 such as physical determinants of health.

With continued reference to FIG. 1, computing device 104 is configured to identify information missing from an identified conditional indicator group. Information may be missing when there is not any information pertaining to a conditional indicator group 128, and/or when there may not be enough information gathered pertaining to a conditional indicator group 128. For instance and without limitation, computing device 104 may determine that a conditional indicator group 128 containing information about a user's nutritional habits does not contain enough information because there are very few photographs contained within the plurality of photographs 108 that have information pertaining to the user's nutritional habits. Computing device 104 is configured to transmit a request to a remote device 116 operated by the human subject, to obtain more information. Computing device 104 transmits the request to a remote device 116 operated by the human subject utilizing any network methodology as described herein. A request to obtain more information may include a series of one or more questions and/or comments for a user to elaborate on. In an embodiment, a request to obtain more information may include a questionnaire, that may contain user responses to questions. In an embodiment, a request to obtain more information may be generated based on one or more expert inputs contained within expert database 124. Computing device 104 receives from the remote device 116 operated by the human subject a response containing at least an element of information. An "element of information," as used in this disclosure, includes any information that is not possessed by computing device 104.

With continued reference to FIG. 1, computing device 104 is configured to generate a classification algorithm 132 utilizing a conditional indicator 120. A "classification algorithm," as used in this disclosure, is a process whereby a computing device 104 derives, from training data, a model for sorting inputs into categories or bins of data. Training data," as used in this disclosure, is data containing correlations that a machine-learning process 152 may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning process 152 *es* as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, a "classification algorithm," as used in this disclosure, is a process whereby a computing device 104 derives, from training data, a model for sorting inputs into categories or bins of data. Training data includes any of the training data as described herein. Classification may be performed using, without limitation, linear classifiers such as without limitation logistic regression and/or naive Bayes classifiers, nearest neighbor classifiers including without limitation k-nearest neighbors classifiers, support vector machines, decision trees, boosted trees, random forest classifiers, and/or neural network-based classifiers.

With continued reference to FIG. 1, classification algorithm 132 may include generating a Naïve Bayes classification algorithm 132. Naïve Bayes classification algorithm 132 generates classifiers by assigning class labels to problem instances, represented as vectors of feature values. Class labels are drawn from a finite set. Naïve Bayes classification algorithm 132 may include generating a family of algorithms that assume that the value of a particular feature is independent of the value of any other feature, given a class variable. Naïve Bayes classification algorithm 132 may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming classification training data into a frequency table. Computing device 104 may then calculate a likelihood table by calculating probabilities of different data entries and classification labels. Computing device 104 utilizes a naïve Bayes equation to calculate a posterior probability for each class. A class containing the highest posterior probability is the outcome of prediction. Naïve Bayes classification algorithm 132 may include a gaussian model that follows a normal distribution. Naïve Bayes classification algorithm 132 may include a multinomial model that is used for discrete counts. Naïve Bayes classification algorithm 132 may include a Bernoulli model that may be utilized when feature vectors are binary. Naïve Bayes classification algorithm 132 utilizes training data and at least a retrieved element of user data as an input to output a user metabolic state. A metabolic state may be identified utilizing a classification label, where a "classification label" as used in this disclosure, includes a label that indicates whether an input belongs to a particular class or not. In an embodiment, a classification label may include an indication as to the metabolic state of the user. For example, a user with hyperthyroidism who is a hyper-metabolizer may be classified to a metabolic state that indicates that the user is a hypermetabolizer, whereas a user who is not active, and does not engage in physical activity may be classified to a metabolic state that indicates that the user is a slow metabolizer.

With continued reference to FIG. 1, classification algorithm 132 may include generating a K-nearest neighbor (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, classification algorithm 132 utilizes a conditional indicator 120 as an input and outputs a conditional profile 136. A "conditional profile," as used in this disclosure, is data including any numerical, character, and/or symbolic data describing the overall health and/or well-being of a human subject. A conditional profile 136 may include information describing one or more suspected conditions that a user may be suffering from. A "condition," as used in this disclosure, is the identification of any state of a user's health. A condition may identify a likelihood or percentage that a user suffers from a specific illness such as a user who has a depressed mood, low energy, and fatigue may have a high likelihood of suffering from an illness of depression. A condition may identify the likelihood of a user suffering from a pre-condition, such as pre-diabetes. A condition may identify a likelihood that a user will develop a disease such as the likelihood that a user will develop heart disease or breast cancer. A condition may identify a health status that may reflect one or more indicators of health. For instance and without limitation, a classification algorithm 132 may utilize a conditional indicator 120 such as pale names to classify the user to a conditional profile 136 that reflects the likelihood that a user has anemia. In yet another non-limiting example, a classification algorithm 132 may utilize a conditional indicator 120 such as breakouts on chin/jawline to classify the user to a conditional profile 136 that reflects the likelihood that a user has a hormone disruption.

With continued reference to FIG. 1, computing device 104 is configured to retrieve an element of user physiological data 140. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin A1-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices 104; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module as described in this disclosure. As a non-limiting example, biological extraction may include a psychological profile; the psychological profile may be obtained utilizing a questionnaire performed by the user.

Still referring to FIG. 1, physiological state data may include genomic data, including deoxyribonucleic acid (DNA) samples and/or sequences, such as without limitation DNA sequences or other genetic sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server may present to user a set of assessment questions designed or intended to evaluate a current state of mind of the user, a current psychological state of the user, a personality trait of the user, or the like; at least a server may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device 116; third-party device 116 may include, without limitation, a server or other device (not shown) that performs automated cognitive, psychological, behavioral, personality, or other assessments. Third-party device 116 may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anaerobic bacterial cultures, fecal short chain fatty acids, beta-glucuronidase, cholesterol, chymotrypsin, fecal color, cryptosporidium EIA, *Entamoeba histolytica*, fecal lactoferrin, Giardia lamblia EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *Campylobacter* species, *Clostridium difficile, Cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albi-*

*cans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as *Ackerman's muciniphila, Anaerotruncus colihominis, bacteriology, Bacteroides vulgates', Bacteroides-Prevotella, Barnesiella* species, *Bifidobacterium longarm, Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, *Oxalobacter formigenes*, parasitology, *Prevotella* species, *Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease-causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen-based breath tests, fructose-based breath tests, *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vasodilation and vasoconstriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androsterone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100. User data may include a profile, such as a psychological profile, generated using previous item selections by the user; profile may include, without limitation, a set of actions and/or navigational actions performed as described in further detail below, which may be combined with biological extraction data and/or other user data for processes such as classification to user sets as described in further detail below.

Still referring to FIG. 1, retrieval of biological extraction may include, without limitation, reception of biological extraction from another computing device 104 such as a device operated by a medical and/or diagnostic professional and/or entity, a user client device, and/or any device suitable for use as a third-party device as described in further detail below. Biological extraction may be received via a questionnaire posted and/or displayed on a third-party device as described below, inputs to which may be processed as described in further detail below. Alternatively or additionally, biological extraction may be stored in and/or retrieved from a user database 144. User database 144 may include any data structure for ordered storage and retrieval of data, which may be implemented as a hardware or software module. A user database 144 may be implemented, without limitation, as a relational database, a key-value retrieval datastore such as a NOSQL database, or any other format or structure for use as a datastore that a person skilled in the art would recognize as suitable upon review of the entirety of this disclosure. A user database 144 may include a plurality of data entries and/or records corresponding to user tests as described above. Data entries in a user database 144 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a user database 144 may reflect categories, cohorts, and/or populations of data consistently with this disclosure. User database 144 may be located in memory of computing device 104 and/or on another device in and/or in communication with system 100.

With continued reference to FIG. 1, and as noted above, retrieval of biological extract may be performed multiple sequential and/or concurrent times, and any process using biological extract as described below may be performed multiple sequential and/or concurrent times; likewise, biological extract may include multiple elements of physiological data, which may be used in combination for any determination and/or other processes as described below.

An element of physiological data may include a user reported element of physiological data. A user reported element of physiological data may include any medical data pertaining to a user, supplied by a user. For example, a user reported element of physiological data may include any previous health history, health records, diagnosis, medications, treatments, major surgeries, complications, and the like that the user may be suffering from. For example, a user reported an element of physiological data may include an anaphylactic reaction to all tree nuts that the user was diagnosed with as a young child. In yet another non-limiting example, a user reported element of physiological data may describe a previous diagnosis such as endometriosis that the user was diagnosed with three years back, and treatments that the user engages in to manage her endometriosis, including supplementation with fish oil and following a gluten free diet. In yet another non-limiting example, a user may provide one or more elements of health history information, such as when a user may select how much of a user's medical records the user seeks to share with computing device 104. For example, a user may prefer to share only the user's hospitalization records and not the user's current medication list. In yet another non-limiting example, a user may seek to share as many records as are available for the user, such as the user's entire vaccination history. In yet another non-limiting example, a user may share health history information that is available to the user, such as when records may become lost or misplaced. An element of physiological data may include an amount of information or certain records based on a user's entire medical record that the user seeks to share and allow system 100 and/or a computing device 104 to have access to. For example, a user may prefer to share only the user's hospitalization records and not the user's current medication list. In yet another non-limiting example, a user may seek to share as many records as are available for the user, such as the user's entire health history. In yet another non-limiting example, a user may not wish to share any information pertaining to a user's health history. In yet another non-limiting example, a user may be unable to share any information pertaining to a user's health history, because the user may be adopted and may not have access to health records, or the user is unable to locate any health records for the user and the like. An element of physiological data may include a user reported self-assessment. A "self-assessment" as used in this disclosure, is any questionnaire that may prompt and/or ask a user for any element of user health history. For instance and without limitation, a self-assessment may seek to obtain information including demographic information such as a user's full legal name, sex, date of birth, marital status, date of last physical exam and the like. A self-assessment may seek to obtain information regarding a user's childhood illness such as if the user suffered from measles, mumps, rubella, chickenpox, rheumatic fever, polio and the like. A self-assessment may seek to obtain any vaccination information and dates a user received vaccinations such as tetanus, hepatitis, influenza, pneumonia, chickenpox, measles mumps and rubella (MMR), and the like. A self-assessment may seek to obtain any medical problems that other doctors and/or medical professionals may have diagnosed. A self-assessment may seek to obtain any information about surgeries or hospitalizations the user experienced. A self-assessment may seek to obtain information about previously prescribed drugs, over-the-counter drugs, supplements, vitamins, and/or inhalers the user was prescribed. A self-assessment may seek to obtain information regarding a user's health habits such as exercise preferences, nutrition and diet that a user follows, caffeine consumption, alcohol consumption, tobacco use, recreational drug use, sexual health, personal safety, family health history, mental health, other problems, other remarks, information pertaining to women only, information pertaining to men only and the like. Computing device 104 is configured to generate the classification algorithm 132 utilizing the element of user physiological data 140.

With continued reference to FIG. 1, computing device 104 is configured to determine a conditional status 148 of a human subject utilizing a conditional profile 136. A "conditional status" as used in this disclosure, is the identification of any health conditions that a user may be and/or is likely to be suffering from. A conditional status 148 may identify a disease likelihood score, defined for the purposes of this disclosure as a quantitative datum that indicates the likelihood that a user has a disease. A likelihood may include a numerical likelihood reported on a scale, and/or may include a likelihood reported based on character values indicating how probable or likely it is that a user has a disease. For instance and without limitation, a conditional status 148 may indicate that a user who has pale lips, a swollen face, and red eyes may have a high likelihood of suffering from a disease such as a common cold. In yet another non-limiting example, a conditional status 148 may indicate that a user who has a very small social network consisting of a few friends, consumes alcohol, and does not exercise has a moderate likelihood of having depression. A conditional status 148 includes a treatment identifier. A "treatment identifier," as used in this disclosure, is an element of data identifying a therapeutic agent and/or remedy, that may correct or lessen a condition identified within a conditional status 148. A treatment identifier may include treatments that include prescription medications, over the counter medications, vitamins, supplements, herbals, nutritional interventions, fitness programs, meditation sequences, yoga classes and the like. For instance and without limitation, computing device 104 may generate for a user with a condition such as the common cold, a treatment identifier that includes chicken and rice soup, along with elderberry supplement and plenty of fluids. In yet another non-limiting example, a treatment identifier may recommend excess consumption of cruciferous vegetables for a user with a condition such as pre-menstrual syndrome (PMS).

With continued reference to FIG. 1, computing device 104 determines the conditional status 148 of a human subject utilizing a machine-learning process 152. A "machine learning process" is a process that automatedly uses a body of data known as "training data" and/or a "training set" to generate an algorithm that will be performed by a computing device 104 and/or module to produce outputs given data provided as inputs; this is in contrast to a non-machine learning software program where the commands to be executed are determined in advance by a user and written in a programming language.

With continued reference to FIG. 1, computing device 104 may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Continuing to refer to FIG. 1, machine-learning algorithms may include supervised machine-learning algorithms. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may utilize a conditional profile 136 as described above as inputs, a conditional status 148 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs. Supervised machine-learning process 152 es may include classification algorithm 132 as defined above.

Still referring to FIG. 1, machine learning process es may include unsupervised processes. An unsupervised machine-learning process 152, as used herein, is a process that derives inferences in datasets without regard to labels; as a result, an unsupervised machine-learning process 152 may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

With continued reference to FIG. 1, machine-learning process 152 as described in this disclosure may be used to generate machine-learning models. A machine-learning model, as used herein, is a mathematical representation of a relationship between inputs and outputs, as generated using any machine-learning process 152 including without limitation any process as described above, and stored in memory; an input is submitted to a machine-learning model once created, which generates an output based on the relationship that was derived. For instance, and without limitation, a linear regression model, generated using a linear regression algorithm, may compute a linear combination of input data using coefficients derived during machine-learning process 152 es to calculate an output datum. As a further non-limiting example, a machine-learning model may be generated by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 1, at least a machine-learning process 152 may include a lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data. Heuristic may include selecting some number of highest-ranking associations and/or training data elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below. Computing device 104 calculates a machine-learning process 152 wherein the machine-learning process 152 utilizes a conditional profile 136 as an input and outputs a conditional status. Computing device 104 determines the conditional status 148 of a human subject utilizing the machine-learning process.

With continued reference to FIG. 1, computing device 104 is configured to transmit the conditional status 148 of a human subject to a remote device 116 operated by an informed advisor. An "informed advisor," as used in this disclosure, includes any individual who may be involved in contributing to the health and well-being of the human subject. An informed advisor may include a physician, doctor, nurse, physician assistant, nurse practitioner, pharmacist, psychiatrist, psychologist, nutritionist, dietician, yoga instructor, meditation teacher, spiritual advisor, church leader, and the like. Computing device 104 receives an input generated by an informed advisor in response to the conditional status 148 of the human subject. In an embodiment, an input generated by an informed advisor may provide background information, confirm information about a user, update information about a user, and/or provide feedback regarding a conditional status. For example, an input generated by a user's nutritional advisor may confirm a disease likelihood contained within a conditional status 148 and indicate that a user does have a Vitamin D deficiency. In yet another non-limiting example, an input generated by an informed advisor may confirm that a treatment identifier contained within a conditional status 148 is appropriate for a user. Computing device 104 updates a conditional status 148 utilizing an input generated by an informed advisor. Updating a conditional status 148 may include updating a disease likelihood score so as to confirm the likelihood of a user disease.

Figure 2:
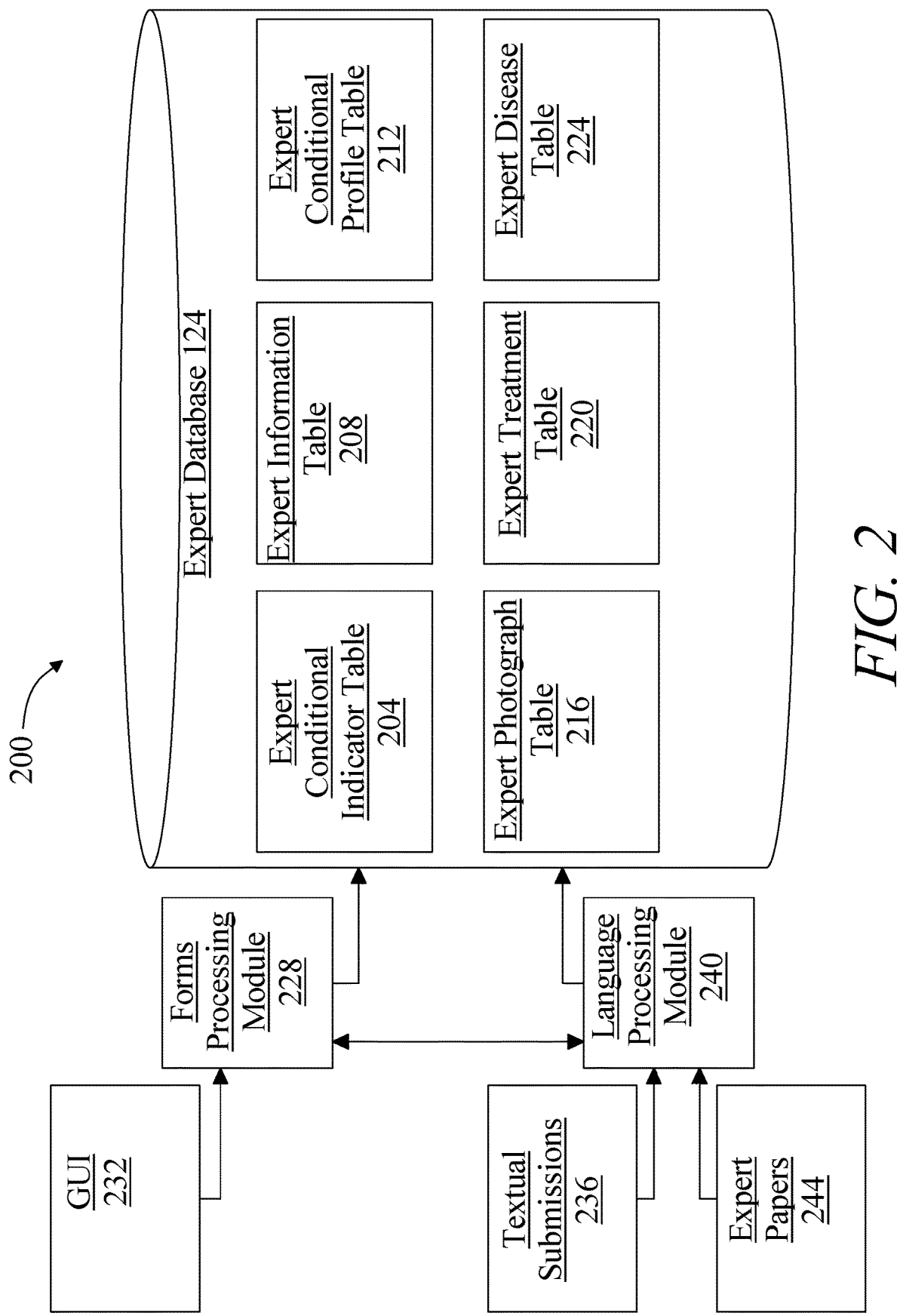
FIG. 2 is a block diagram illustrating an exemplary embodiment of an expert database.

Referring now to FIG. 2, an exemplary embodiment 200 of expert database 124 is illustrated. Expert database 124 may, as a non-limiting example, organize data stored in the expert database 124 according to one or more database tables. One or more database tables may be linked to one another by, for instance, common column values. For instance, a common column between two tables of expert database 124 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in expert database 124 may include, as a non-limiting example, an expert conditional indicator table 204; expert conditional indicator 204 may include expert information relating to conditional indicator 120. One or more database tables in expert database 124 may include, as a non-limiting example, an expert information table 208; expert information table 208 may include expert information relating to any information necessary within system 100, including for example, information relating to conditional indicators. One or more database tables in expert database 124 may include, expert conditional profile 212; expert conditional profile table 212 may include expert information relating to conditional profile 136. One or more database tables in expert database 124 may include, expert photograph table 216; expert photograph table 216 may include expert information relating to photographs. One or more database tables in expert database 124 may include, expert treatment table 220; expert treatment table 220 may include expert information relating to treatments. One or more database tables in expert database 124 may include expert disease table 224; expert disease table 224 may include expert information relating to diseases.

In an embodiment, and still referring to FIG. 2, a forms processing module 228 may sort data entered in a submission via a graphical user interface 232 receiving expert submissions by, for instance, sorting data from entries in the graphical user interface 232 to related categories of data; for instance, data entered in an entry relating in the graphical user interface 232 to a conditional indicator 120 such as social determinants of health, which may be provided to expert conditional indicator 120 table 204, while data entered in an entry relating to recommended treatments for acne vulgaris, which may be provided to expert disease table 224. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submission 236, such as accomplished by filling out a paper or PDF form and/or submitting narrative information, may likewise be processed using language processing module.

Still referring to FIG. 2, a language processing module 240 may include any hardware and/or software module. Language processing module 240 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams" where all sequences of n consecutive characters are considered. Any or all possible sequences of tokens or words may be stored as "chains" for example for use as a Markov chain or Hidden Markov Model.

Still referring to FIG. 2 language processing module 240 may compare extracted words to categories of data to be analyzed; such data for comparison may be entered on computing device 104 as described above using expert data inputs or the like. In an embodiment, one or more categories may be enumerated, to find total count of mentions in such documents. Alternatively or additionally, language processing module 240 may operate to produce a language processing model. Language processing model may include a program automatically generated by at least a server and/or language processing module 240 to produce associations between one or more words extracted from at least a document and detect associations, including without limitation mathematical associations, between such words, and/or associations between such words and other elements of data analyzed, processed and/or stored by system 100. Associations between language elements, may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of data; positive or negative indication may include an indication that a given document is or is not indicating a category of data.

Still referring to FIG. 2, language processing module 240 and/or computing device 104 may generate the language processing model by any suitable method, including without limitation a natural language processing classification algorithm 132; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 240 may combine two or more approaches. For instance, and without limitation, machine-learning program may use a combination of Naive-Bayes (NB), Stochastic Gradient Descent (SGD), and parameter grid-searching classification techniques; the result may include a classification algorithm 132 that returns ranked associations.

Continuing to refer to FIG. 2, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 2, language processing module 240 may use a corpus of documents to generate associations between language elements in a language processing module 240, and computing device 104 may then use such associations to analyze words extracted from one or more documents. Documents may be entered into computing device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, computing device 104 may automatically obtain the document using such an identifier, for instance by submitting a request to a database or compendium of documents such as JSTOR as provided by Ithaka Harbors, Inc. of New York.

With continued reference to FIG. 2, data may be extracted from expert papers 244, which may include without limitation publications in medical and/or scientific journals, by language processing module 240 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

Figure 3:
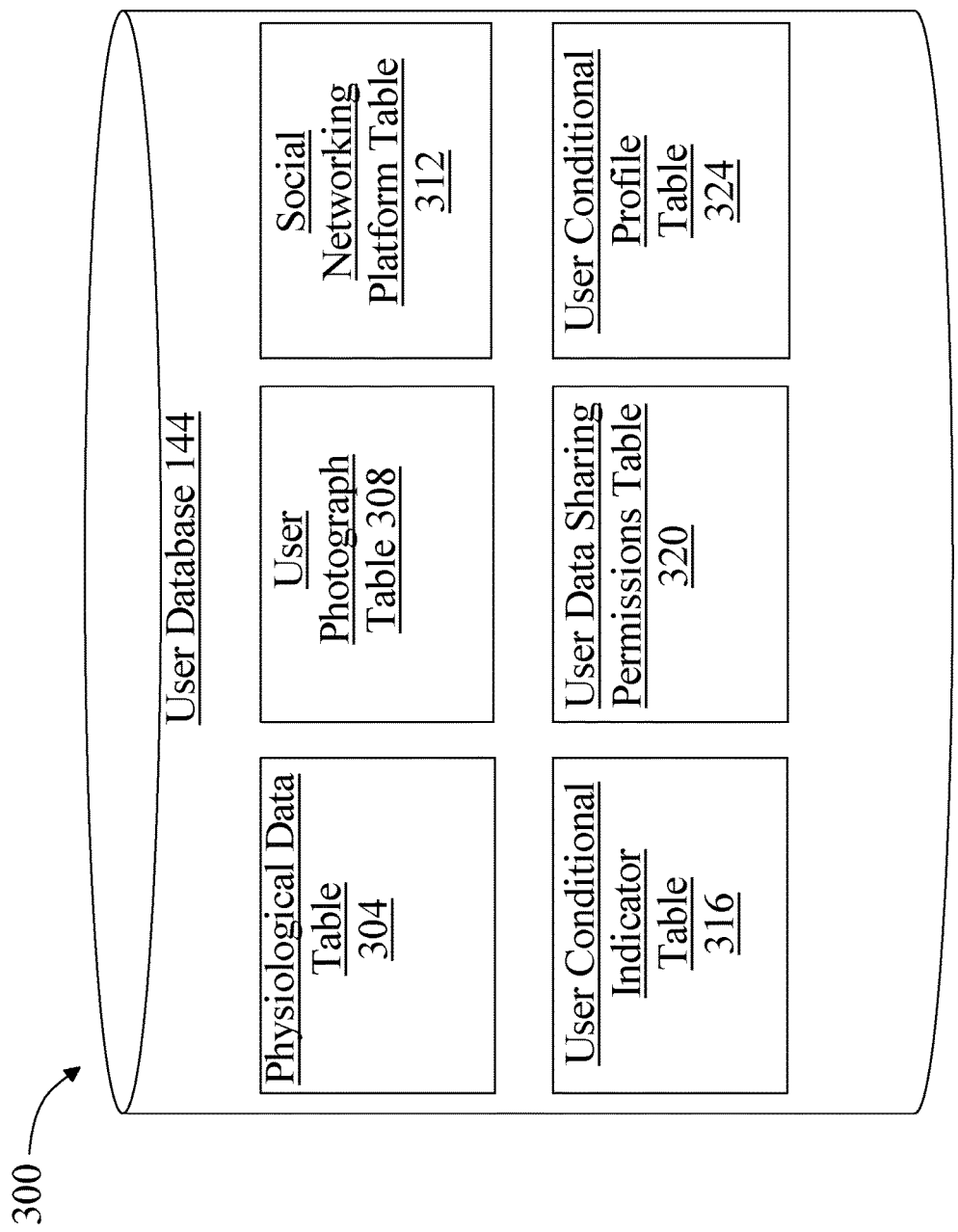
FIG. 3 is a block diagram illustrating an exemplary embodiment of a user database.

Referring now to FIG. 3, an exemplary embodiment 300 of user database 144 is illustrated. User database 144 may be implemented as any data structure suitable for use as expert database 124 as described above in more detail. One or more tables contained within user database 144 may include user physiological data table 304; user physiological data table 304 may include one or more elements of physiological data, one or more biological extractions, and/or one or more elements of user health information. One or more tables contained within user database 144 may include user photograph table 308; user photograph table 308 may include one or more photographs of a user. One or more tables contained within user database 144 may include social networking platform table 312; social networking platform table 312 may include information pertaining to one or more social networking platforms that a user may engage with. One or more tables contained within user database 144 may include conditional indicator table 316; conditional indicator table 316 may include information pertaining to one or more conditional indicator 120 for a user. One or more tables contained within user database 144 may include user data sharing permissions table 320; user data sharing permissions table 320 may include information pertaining to data a user may share with system 100 and/or with social networking platforms. One or more tables contained within user database 144 may include user conditional profile table 324; user conditional profile table 324 may include information pertaining to conditional profiles 136 relating to a user.

Figure 4:
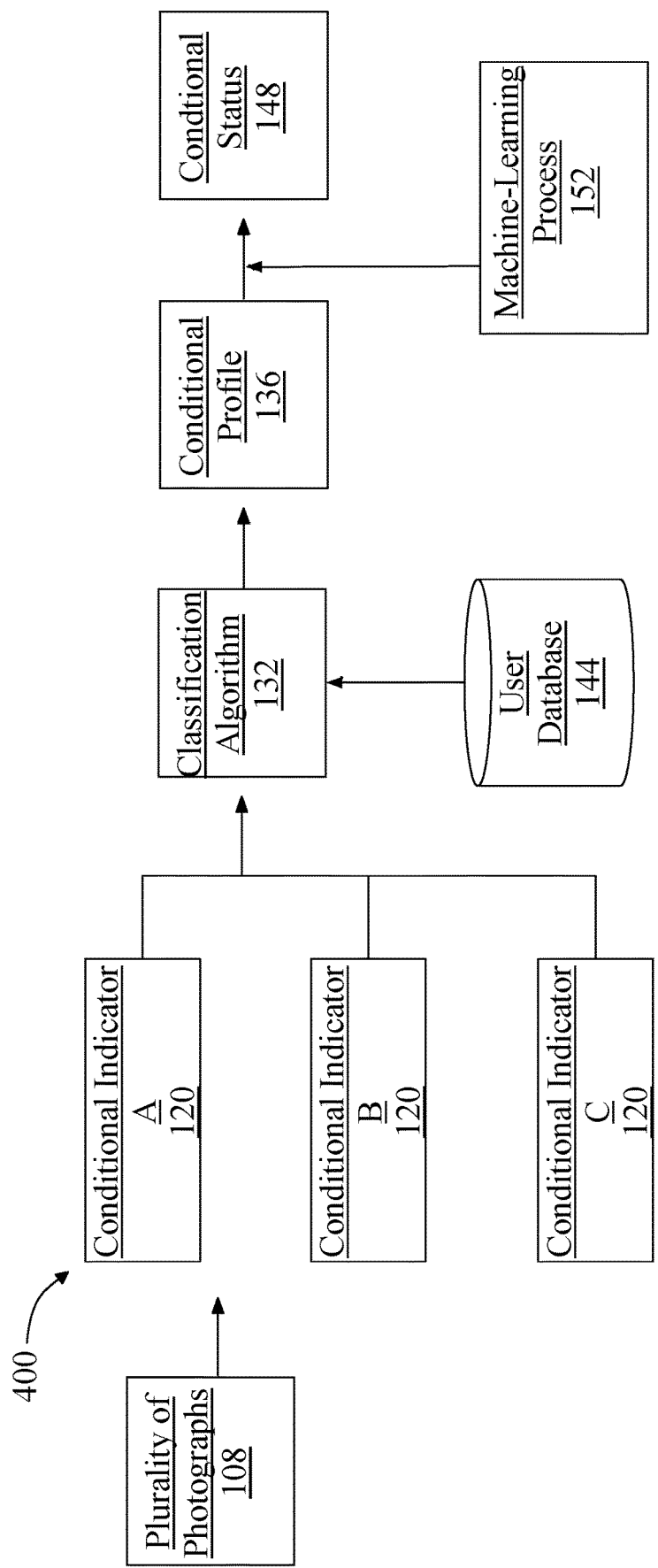
FIG. 4 is a diagrammatic representation of aspects of determining a conditional status.

Referring now to FIG. 4, an exemplary embodiment 400 of generating a conditional status 148 is generated. Computing device 104 receives a plurality of photographs 108, which may be received from a plurality of sources. For example, photographs may be received from user inputs from remote device 116. Photographs may be received at an image capture device 112 located on computing device 104. Photographs may be received from one or more social networking platforms as described above in more detail. Computing device 104 analyzes a plurality of photographs 108 to identify one or more conditional indicator 120 describes any determinant of a user's health. In an embodiment, computing device 104 may generate a plurality of conditional indicator 120. For instance and without limitation, computing device 104 may examine a plurality of photographs 108 pertaining to a human subject and generate a first conditional indicator 120 "A" that indicates a user drinks alcohol, a second conditional indicator "B" that indicates the user engages in physical activity, and a third conditional indicator 120 "C" that indicates a the user orders takeout meals from restaurants as opposed to cooking meals at home. In an embodiment, one or more conditional indicator 120 may be generated based on input contained within expert database 124. Computing device 104 utilizes conditional indicator 120 in combination with a classification algorithm 132 to generate a conditional profile 136. Classification algorithm 132 includes any of the classification algorithm 132 as described above in more detail. Conditional profile includes any of the conditional profile 136 as described above in more detail in reference to FIG. 1. Computing device 104 utilizes a conditional profile 136 to determine a conditional status 148 of the user. A conditional status 148 may indicate the likelihood that a user has a particular disease. For example, a conditional status 148 may indicate that a user has a low likelihood of having necrotizing fasciitis, but a high likelihood of having urticaria. A conditional status 148 may contain a treatment identifier, which may identify one or more treatments available for a disease identified within a disease likelihood score. In an embodiment, a conditional status 148 may be generated based on information contained within expert database 124. In an embodiment, a conditional status 148 may be generated utilizing one or more machine-learning process 152*es*. A machine-learning process 152 includes any of the machine-learning process 152*es* as described above in more detail in reference to FIG. 1.

Figure 5:
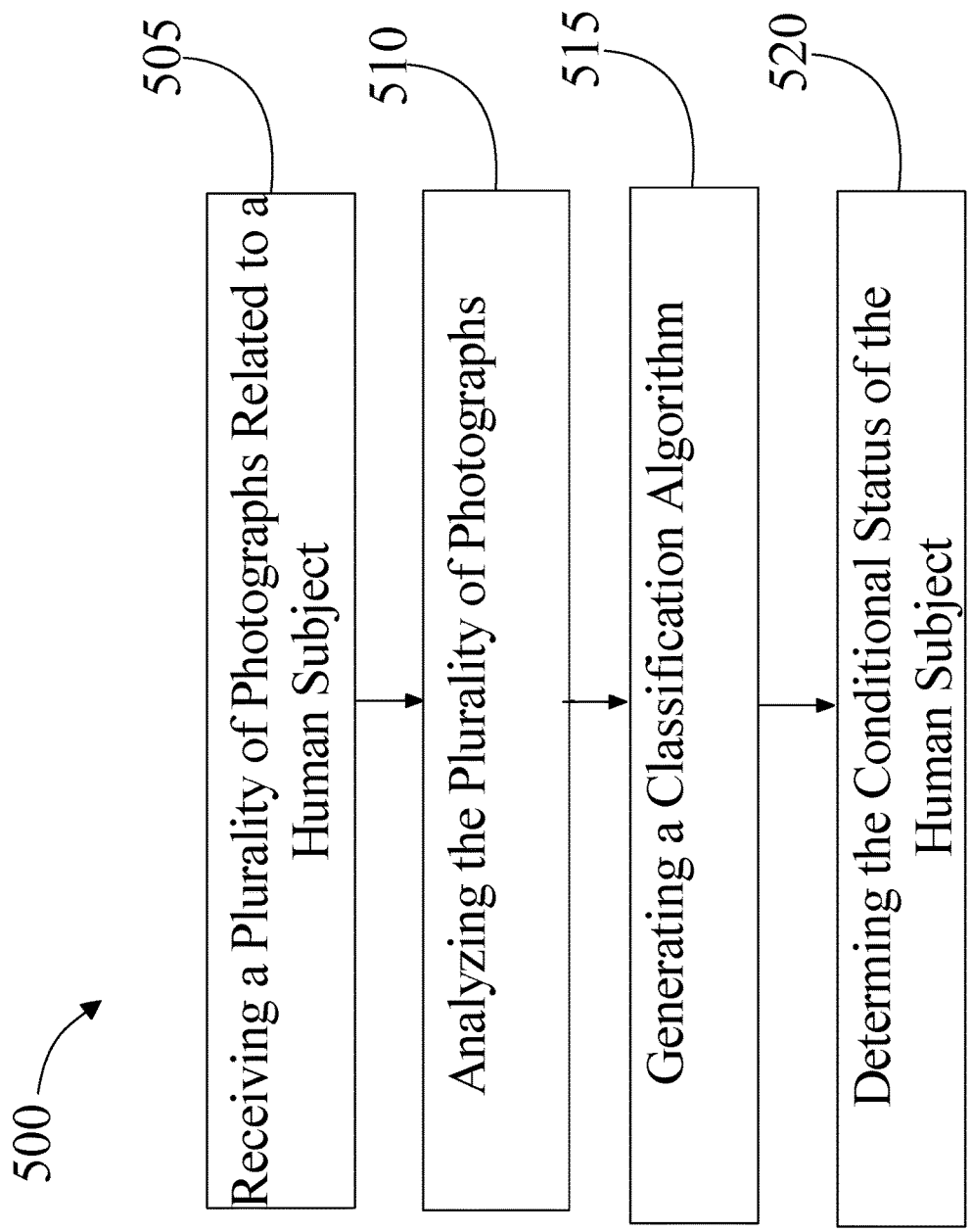
FIG. 5 is a process flow diagram illustrating an exemplary embodiment of an artificial intelligence method of analyzing imagery.

Referring now to FIG. 5, an exemplary embodiment 500 of an artificial intelligence method of analyzing imagery is illustrated. At step 505, a computing device 104 receives a plurality of photographs 108 related to a human subject. A photograph, includes any of the photographs as described above in more detail in reference to FIG. 1. Computing device 104 receives at an image capture device 112 located on computing device 104 a wireless transmission from a remote device 116 containing a plurality of photographs 108 related to the human subject. An image capture device 112 includes any of the image capture device 112 as described above in more detail in reference to FIG. 1. Computing device 104 receives a wireless transmission from a remote device 116 utilizing any network methodology as described herein. In an embodiment, an image capture device 112 may be located on a remote device 116. In such an instance, a user may capture one or more photographs of the user and/or photographs related to the user as described above. A user may transmit the plurality of photographs 108 to computing device 104 utilizing any network methodology as described herein. Computing device 104 receives a plurality of photographs 108 related to a human subject from a social networking platform. A social networking platform includes any of the social networking platforms as described above in more detail in reference to FIG. 1. In an embodiment, a user may specify requirements relating to a social networking platform, indicating what social networking platforms computing device 104 may receive photographs from, dates of photographs and what dates photographs may be received from. One or more user preferences regarding social networking platforms may be stored in user database 144 as described above in more detail in reference to FIGS. 1-4. In an embodiment, computing device 104 may receive a plurality of photographs 108 from a social networking platform and/or from a website by scraping data utilizing a web scraper, as described above in more detail in reference to FIG. 1.

With continued reference to FIG. 5, at step 510, a computing device 104 analyzes a plurality of photographs 108 to identify a conditional indicator 120 contained within the plurality of photographs 108. A conditional indicator 120 includes any of the conditional indicator 120 as described above in more detail in reference to FIGS. 1-4. A conditional indicator 120 describes any determinant of health of a user, including any factor that can have an impact on one's health and wellness. A determinant of health may include factors such as where a user lives, the state of a user's home environment, genetics, income, education level, social relationships with family, friends, acquaintances and the like, race, gender, age, nutrition, social status community involvement and/or engagement, major life events, physical activity levels, smoking status, alcohol and drug use, access to healthcare, health behaviors, and the like. Computing device 104 identifies conditional indicator 120 contained within a plurality of photographs utilizing input contained within expert database 124. For instance and without limitation, computing device 104 may identify conditional indicators contained within a plurality of photographs 108 that indicate the user has a large social network of friends, the user does not drink alcohol or smoke, and the user has a butterfly shaped rash across the bridge of the user's nose and cheeks.

With continued reference to FIG. 5, computing device 104 identifies a conditional indicator group 128 identified within a plurality of photographs 108. A conditional indicator group 128, includes any of the conditional indicator group 128 as described above in more detail in reference to FIG. 1. A conditional indicator group may contain one or more shared determinants of health. For example, a conditional indicator group may include socioeconomic determinants of health, behavioral determinants of health, environmental determinants of health, physiological determinants of health, genetic determinants of health, epigenetic determinants of health and the like. Computing device 104 identifies a conditional indicator group 128 utilizing input contained within expert database 124. Computing device 104 generates a label identifying a conditional indicator group 128. A label includes any of the labels as described above in more detail in reference to FIG. 1. Computing device 104 identifies information missing from an identified group of a conditional indicator 120. For instance and without limitation, a conditional indicator group 128 such as behavioral determinants of health may only contain information that identifies the user as a smoker. However, information such as other behavioral determinants of health may be missing, including information regarding alcohol use, exercise frequency, supplement use, meditation practices, yoga practices and the like. Computing device 104 transmits a request to a remote device 116 operated by the human subject to obtain more information. Such a request may be transmitted utilizing any network methodology as described herein. Computing device 104 receives from the remote device 116 operated by the human subject a response containing at least an element of information. Such information received from the remote device 116 operated by the human subject may be utilized to generate classification algorithm. In an embodiment, such information received from the remote device 116 may be stored within user database 144.

With continued reference to FIG. 5, at step 515 a computing device 104 generates a classification algorithm 132 utilizing a conditional indicator 120. A classification algorithm 132 includes any of the classification algorithm 132 as described above in more detail in reference to FIG. 1. In an embodiment, computing device 104 may select a classification algorithm 132 utilizing input contained within expert database 124. A classification algorithm 132 utilizes a conditional indicator 120 as an input and outputs a conditional profile 136. A conditional profile 136 includes any of the conditional profile 136 as described above in more detail in reference to FIG. 1. A conditional profile 136 describes the overall health and/or well-being of a human subject. For example, a conditional profile 136 may describe on a sliding scale, the overall health and/or well-being of a human subject. For example, a conditional profile 136 may specify that a user is in good physical health but needs to work on emotional health because the user has very few friends and does not engage in many hobbies. In yet another non-limiting example, a conditional profile 136 may describe that a user is in poor physical health as noted from conditional indicators contained within a plurality of photographs 108 as the user appears to have puffy eyes, bloated cheeks, a pale demeanor, and looks to be exhausted. Computing device 104 is configured to retrieve an element of user physiological data 140 that may provide information utilized to generate a conditional profile 136. An element of user physiological data 140 includes any of the elements of user physiological data 140 as described above in more detail. For instance and without limitation, an element of user physiological data 140 may include a stool sample analyzed for one or more strains of bacteria inside a user's gut. In yet another non-limiting example, an element of user physiological data 140 may include a urine sample analyzed for one or more nutrients such as iodine. Computing device 104 generates a classification algorithm 132 utilizing an element of user physiological data 140. An element of user physiological data 140 may be stored in user database 144, as described above in more detail in reference to FIG. 1.

With continued reference to FIG. 5, at step 520, computing device 104 determines a conditional status 148 of a human subject utilizing the conditional profile 136. A conditional status 148, includes any of the conditional status 148*es* as described above in more detail in reference to FIG. 1. A conditional status 148 identifies any health conditions that a user may be and/or is likely to be suffering from. A health condition includes any of the health conditions as described above in more detail in reference to FIG. 1. Computing device 104 determines a conditional status 148 utilizing information contained within a conditional profile 136, indicating the overall health and/or well-being of a user. For instance and without limitation, a conditional profile 136 may indicate that a user has a very small social network, the user has very few hobbies, the user sleeps a lot, and the user has low Vitamin D. In such an instance, computing device 104 may utilize the information contained within the user's conditional profile 136 to determine a conditional status that indicates the user may be suffering from depression. A conditional status 148 may be determined utilizing input contained within expert database 124. Computing device 104 generates a conditional status 148 that contains a disease likelihood score. A disease likelihood score includes any of the disease likelihood scores as described above in more detail in reference to FIG. 1. Computing device 104 generates a conditional status 148 that contains a treatment identifier. A treatment identifier includes any of the treatment identifies as described above in more detail in reference to FIG. 1. Computing device 104 determines a conditional status by calculating a machine-learning process 152. A machine-learning process 152 includes any of the machine-learning process 152*es* as described above in more detail in reference to FIG. 1. A machine-learning process 152 utilizes a conditional profile 136 as an input and outputs a conditional status 148. Computing device 104 determines the conditional status 148 of a human subject utilizing a machine-learning process 152.

With continued reference to FIG. 5, computing device 104 transmits a conditional status 148 of a human subject to a remote device 116 operated by an informed advisor. An informed advisor includes any of the informed advisors as described above in more detail in reference to FIG. 1. A conditional status 148 may be transmitted from computing device 104 to a remote device 116 operated by an informed advisor utilizing any network methodology as described herein. Computing device 104 receives an input generated by the informed advisor in response to the conditional status 148 of the human subject. In an embodiment, an input generated by the informed advisor may provide more information about the human subject, may confirm a treatment identified within the conditional status 148, and/or may confirm or deny a disease identified within a conditional status 148. Computing device 104 updates a conditional status utilizing input generated by an informed advisor.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
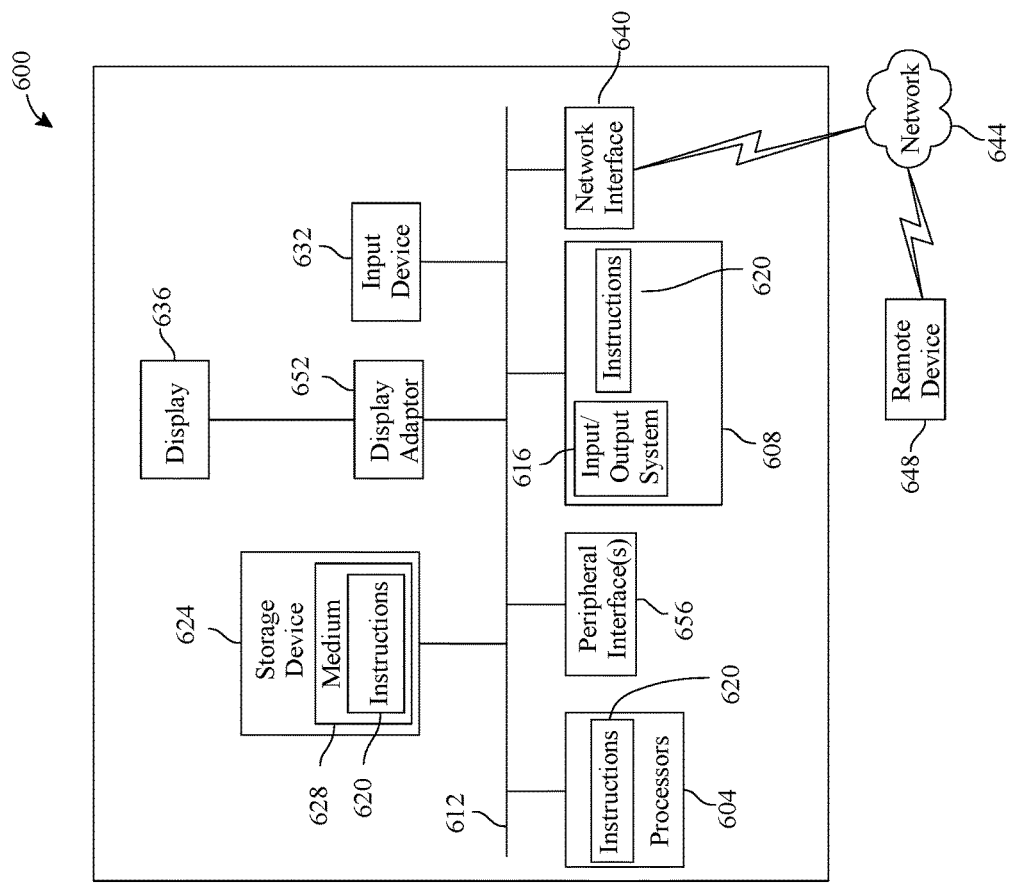
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An artificial intelligence system for analyzing imagery, the system comprising a computing device, the computing device designed and configured to:
receive a plurality of photographs related to a human subject;
receive an element of user physiological data;
analyze the plurality of photographs to identify a conditional indicator contained within the plurality of photographs;

generate a classification algorithm, wherein the classification algorithm utilizes:
the conditional indicator and the element of physiological data as inputs, wherein the element of physiological data is classified to a disease state category from a plurality of disease state categories; and
outputs a conditional profile; and
determine a conditional status of the human subject utilizing the conditional profile.

2. The system of claim 1, wherein the computing device is further configured to receive at an image capture device located on the computing device a wireless transmission from a remote device containing the plurality of photographs related to a human subject.

3. The system of claim 1, wherein the computing device is further configured to receive the plurality of photographs related to the human subject from a social networking platform.

4. The system of claim 1, wherein the computing device is further configured to:
identify a conditional indicator group identified within the plurality of photographs; and
generate a label, identifying the conditional indicator group.

5. The system of claim 4, wherein the computing device is further configured to:
identify information missing from a conditional indicator group;
transmit a request to a remote device operated by the human subject, to obtain more information relating to the conditional indicator group; and
receive from the remote device operated by the human subject a response containing at least an element of information.

6. The system of claim 1, wherein the computing device is further configured to:
perform a machine-learning process, wherein the machine-learning process utilizes the conditional profile as an input and outputs the conditional status; and
determine the conditional status of the human subject utilizing the machine-learning process.

7. The system of claim 1, wherein the conditional status further comprises a disease likelihood score.

8. The system of claim 1, wherein the conditional status further comprises a treatment identifier.

9. The system of claim 1, wherein the computing device is further configured to:
transmit the conditional status of the human subject to a remote device operated by an informed advisor;
receive an input submitted to the remote device in response to the conditional status of the human subject; and
update the conditional status utilizing the input.

10. An artificial intelligence method of analyzing imagery, the method comprising:
receiving by a computing device, a plurality of photographs related to a human subject;
receiving by the computing device, an element of user physiological data;
analyzing by the computing device, the plurality of photographs to identify a conditional indicator contained within the plurality of photographs;
generating by the computing device, a classification algorithm utilizing the conditional indicator, wherein the classification algorithm utilizes the conditional indicator and the element of physiological data as inputs, wherein the element of physiological data is classified to a disease state category from a plurality of disease state categories; and
outputs a conditional profile; and
determining by the computing device, a conditional status of the human subject utilizing the conditional profile.

11. The method of claim 10, wherein receiving the plurality of photographs further comprises receiving at an image capture device located on the computing device a wireless transmission from a remote device containing the plurality of photographs related to a human subject.

12. The method of claim 10, wherein receiving the plurality of photographs related to the human subject further comprises receiving the plurality of photographs related to the human subject from a social networking platform.

13. The method of claim 10, wherein analyzing the plurality of photographs further comprises:
identifying a conditional indicator group identified within the plurality of photographs; and
generating a label, identifying the conditional indicator group.

14. The method of claim 13 further comprising:
identifying information missing from a conditional indicator group;
transmitting a request to a remote device operated by the human subject, to obtain more information relating to the conditional indicator group; and
receiving from the remote device operated by the human subject a response containing more information.

15. The method of claim 10, wherein determining the conditional status further comprises:
calculating a machine-learning process, wherein the machine-learning process utilizes the conditional profile as an input and outputs the conditional status; and
determining the conditional status of the human subject utilizing the machine-learning process.

16. The method of claim 10, wherein the conditional status further comprises a disease likelihood score.

17. The method of claim 10, wherein the conditional status further comprises a treatment identifier.

18. The method of claim 10 further comprising:
transmitting the conditional status of the human subject to a remote device operated by an informed advisor;
receiving an input generated by the informed advisor in response to the conditional status of the human subject; and
updating the conditional status utilizing the input generated by the informed advisor.

\* \* \* \* \*